United States Patent
Johnson

(10) Patent No.: US 11,242,322 B2
(45) Date of Patent: Feb. 8, 2022

(54) TRIFLAZOLES AND METHODS OF MAKING THE SAME

(71) Applicant: Trinapco, Inc., Oakland, CA (US)

(72) Inventor: Martin Reid Johnson, Piedmont, CA (US)

(73) Assignee: Trinapco, Inc., Oakland, CA (US)

( * ) Notice: Subject to any disclaimer, the term of this patent is extended or adjusted under 35 U.S.C. 154(b) by 0 days.

(21) Appl. No.: 17/064,181

(22) Filed: Oct. 6, 2020

(65) Prior Publication Data

US 2021/0238142 A1    Aug. 5, 2021

Related U.S. Application Data

(60) Provisional application No. 62/968,243, filed on Jan. 31, 2020.

(51) Int. Cl.
  *C07D 233/60* (2006.01)
  *C07D 231/12* (2006.01)

(52) U.S. Cl.
  CPC ......... *C07D 233/60* (2013.01); *C07D 231/12* (2013.01)

(58) Field of Classification Search
  CPC .................. C07D 233/60; C07D 231/12
  See application file for complete search history.

(56) References Cited

U.S. PATENT DOCUMENTS

2002/0009635 A1    1/2002    Michot et al.

FOREIGN PATENT DOCUMENTS

| EP | 3412659 A1 | 12/2018 |
| JP | 2014127354 A | 7/2014 |
| JP | 2019156781 A | 9/2019 |

OTHER PUBLICATIONS

Moiseev, et al. Russian Chemical Bulletin, International Edition, vol. 54, No. 8, Aug. 2005, pp. 1948-1953.*
Garg, et al., "Trifluoromethanesulfonamide derivatives of azoles", Journal of Fluorine Chemistry, 2011, vol. 132, No. 4, pp. 241-243.
Korean Intellectual Property Office (ISA), International Search Report and Written Opinion iissued in corresponding International Patent Application No. PCT/US2020/054404, dated Mar. 8, 2021.

* cited by examiner

*Primary Examiner* — Shawquia Jackson
(74) *Attorney, Agent, or Firm* — Duane Morris LLP

(57) ABSTRACT

Methods for producing triflazoles or related derivatives thereof, and the resulting products are provided. For example, triflazoles can be prepared by reaction of trifluoromethanesulfonyl fluoride with an azole or azolate salt. Yields up to 78% are obtained. Triflazoles can be prepared by the reaction of a trifluoromethanesulfonyl fluoride with an N-silylazole in the presence of a basic catalyst. Yields up to 97% are obtained.

25 Claims, 1 Drawing Sheet

TRIFLAZOLES AND METHODS OF MAKING THE SAME

PRIORITY CLAIM AND CROSS-REFERENCE

This application claims the benefit of U.S. Provisional Application No. 62/968,243, filed Jan. 31, 2020, which is expressly incorporated by reference herein in its entirety.

FIELD OF THE INVENTION

The disclosure relates to chemical synthesis of azole derivatives generally. More particularly, the disclosed subject matter relates to a process for producing triflazoles or related derivatives thereof, and the resulting triflazoles and/or derivatives thereof.

BACKGROUND

The conversion of a phenol or enolate functional group to a trifluoromethanesulfonyl ether ("triflate") is known in the fine chemical industry. Two types of reagents are most used: trifluoromethanesulfonic anhydride ($Tf_2O$), and aromatic triflimides such as N,N-bis(trifluoromethanesulfonyl)aniline ($PhNTf_2$) and N,N-bis(trifluoromethanesulfonyl)-5-chloro-2-aminopyridine (the "Comins reagent"). Both of these reagent groups derive from the industrial feedstock trifluoromethanesulfonyl fluoride ($CF_3SO_2F$). $CF_3SO_2F$ is produced at scale using the Simons electrochemical process from $CH_3SO_2F$ or $CH_3SO_2Cl$, in turn made from methane and sulfuryl chloride. $CF_3SO_2F$ itself is a highly toxic gas and although it is known as a triflating agent for phenolic compounds, it is presently considered unsuitable for production of fine chemicals. $Tf_2O$ offers some improvement over $CF_3SO_2F$ in that it is a liquid at room temperature, and is less toxic. However, $Tf_2O$ itself is prepared from $CF_3SO_2F$ in an expensive multi-step process. $Tf_2O$ is noxious, prone to hydrolysis, and it reacts with some common solvents like THF. The triflimides are preferred as triflating agents. They are bench-stable compounds, prepared from $Tf_2O$, that react with phenols at room temperature, and enolates at low temperature. The main drawback of the triflimide reagents is their cost. It takes four moles of $CF_3SO_2F$ and several steps to produce one mole of triflimide, although a recent Chinese patent (CN110627691) claims to reduce this to two moles and one step.

These two classes of triflating agents are, however, not the only choices. In 1970, the reagent 1-(trifluoromethanesulfonyl)imidazole ("$CF_3SO_2Im$") was prepared from imidazole and $Tf_2O$, and shown to react with phenols at 20-90° C. to give the phenolic triflates in good yield (Effenberger, F.; Mack, K. E. Tetrahedron Letters 1970, 11, 3947-3948). $CF_3SO_2Im$ is mentioned about thirty times in the in the patent literature: As a triflating agent for protic amines and phenolic compounds, as a coupling agent, as a graphene dopant, and in the production of lithium battery electrolytes. In the non-patent literature, $CF_3SO_2Im$ is mentioned as a successful reactant only six times since 1970.

SUMMARY

The present disclosure provides methods for producing triflazoles or related derivatives thereof, and the resulting products.

In accordance with some embodiments, the present disclosure provides methods for obtaining a triflazole by reaction of a trifluoromethanesulfonyl fluoride ($CF_3SO_2F$) with an azole, an azole anion compound ("azolate"), an N-silylazole, or a combination thereof. Examples of a suitable azole, an azole anion compound, or an N-silyazole are given in the

DETAILED DESCRIPTION

The reaction or reactions described herein may be optionally in the presence of an aprotic solvent. Examples of suitable aprotic solvents are given in the Detailed Description. The reactants may be suspended or dissolved in the solvent in some embodiments.

In some embodiments, the azole anion compound or azolate salt has a metal cation. Examples of a suitable metal are included in the Detailed Description.

In some embodiments, the azolate salt is derived separately from the free azole and a protic or aprotic base, or in situ from the free azole and an aprotic base. The terms "protic" and "aprotic" are defined in the Detailed Description. Examples of suitable bases are given in the Detailed Description.

In some embodiments, the azolate salt is derived in situ from the protic azole as the base, wherein the protic azole reacts with itself to produce an azolium azolate.

In some embodiments, the azolate salt is derived in situ from an N-silylazole having an azole base structure. For example, the N-silylazole is an N-(trimethylsilyl)azole in some embodiments.

In some embodiments, the azolate salt is derived in situ from an N-silylazole having an azole base structure in the presence of a catalyst. Examples of suitable catalysts are given in the Detailed Description.

In accordance with some embodiments, an exemplary method comprises reacting $CF_3SO_2F$ with an N-silylazole, and isolating a triflazole, where the N-silylazole has an azole base structure. The azole base structure is protic when in a free form.

Examples of the azole base structure or azole includes, but are not limited to, imidazole, pyrazole, 1,2,4-triazole, benzimidazole, benzotriazole, indazole, 2-methylimidazole, 2-methylbenzimidazole, 3,5-dimethylpyrazole, and their substituted derivatives.

The N-silylazole may be an N-(trialkylsilyl)azole such as an N-(trimethylsilyl)azole.

$CF_3SO_2F$ may be reacted with the N-silylazole in the presence of a catalyst, and/or optionally in the presence of an aprotic solvent as described herein. The catalyst can be a basic catalyst. The catalyst or the basic catalyst are described herein. In some embodiments, the catalyst or the basic catalyst comprises a compound containing reactive fluoride as described herein. In some embodiments, the catalyst is a protic azole or its azolate anion compound.

In some embodiments, the catalyst is basic and comprises an aprotic organic base, which may be selected from tertiary amine, an amidine such as a bicyclic amidine, an isothiourea, a phosphazene, a guanidine, and combinations thereof.

In some embodiments, the catalyst is basic and comprises a compound selected from a metal carbonate, a metal fluoride, a metal hydride, alkyllithium, a Grignard reagent, a hydroxide, an alkoxide anion compound, and a combination thereof.

In some embodiments, the catalyst contains reactive fluoride. Examples of suitable catalysts containing reactive fluoride are given in the Detailed Description.

In accordance with some embodiments, an exemplary method comprises reacting $CF_3SO_2F$ with an azole or an azolate salt of the azole, wherein the azole in a free form is protic; and isolating a triflazole. The azole base structure is a suitable azole as described herein.

In some embodiments, the azolate salt has a cation of a metal selected from the group consisting of lithium, sodium, potassium, cesium, magnesium, and a combination thereof. In some embodiments, the azolate salt is derived from the azole and a metallic base selected from a metal hydride, a metal alkoxide, a metal hydroxide, a metal carbonate, a metal fluoride, an alkyllithium, a Grignard reagent, and a combination thereof. For example, the azolate salt may be derived from the azole and a metal carbonate, the metal being selected from the group consisting of lithium, sodium, potassium, cesium, magnesium, and a combination thereof. The azolate salt may also be derived from the azole and a metal fluoride, and the metal in the meal fluoride can be sodium, potassium, cesium, or a combination thereof. In some embodiments, the azolate salt is derived from the azole and an aprotic base, or the azole itself as the base. The azolate salt may be derived from azole and an aprotic organic base as described herein.

In some embodiments, $CF_3SO_2F$ is reacted with the azole at a pressure at or below atmosphere pressure.

Examples of a resulting compound include, but are not limited to, 1-(trifluoromethanesulfonyl)-1,2,4-triazole, 1-(trifluoromethanesulfonyl)benzimidazole, 1-(trifluoromethanesulfonyl)benzotriazole, 1-(trifluoromethanesulfonyl)pyrazole, 1-(trifluoromethanesulfonyl)-2-methylimidazole, 1-(trifluoromethanesulfonyl)-3,5-dimethylpyrazole.

BRIEF DESCRIPTION OF THE DRAWINGS

The present disclosure is best understood from the following detailed description when read in conjunction with the accompanying drawings. It is emphasized that, according to common practice, the various features of the drawings are not necessarily to scale. On the contrary, the dimensions of the various features are arbitrarily expanded or reduced for clarity. Like reference numerals denote like features throughout specification and drawings.

DETAILED DESCRIPTION

Figure 1:
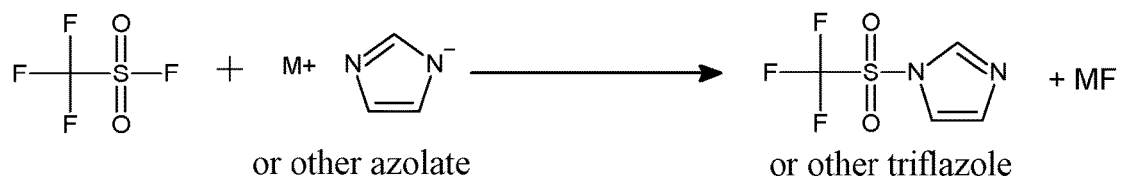
FIG. 1 illustrates an exemplary method for preparing a triflazole in accordance with some embodiments.

For purposes of the description hereinafter, it is to be understood that the embodiments described below may assume alternative variations and embodiments. It is also to be understood that the specific articles, compositions, and/or processes described herein are exemplary and should not be considered as limiting.

In the present disclosure the singular forms "a," "an," and "the" include the plural reference, and reference to a particular numerical value includes at least that particular value, unless the context clearly indicates otherwise. Thus, for example, a reference to "a ring structure" is a reference to one or more of such structures and equivalents thereof known to those skilled in the art, and so forth. When values are expressed as approximations, by use of the antecedent "about," it will be understood that the particular value forms another embodiment. As used herein, "about X" (where X is a numerical value) preferably refers to ±10% of the recited value, inclusive. For example, the phrase "about 8" preferably refers to a value of 7.2 to 8.8, inclusive; as another example, the phrase "about 8%" preferably (but not always) refers to a value of 7.2% to 8.8%, inclusive. Where present, all ranges are inclusive and combinable. For example, when a range of "1 to 5" is recited, the recited range should be construed as including ranges "1 to 4", "1 to 3", "1-2", "1-2 & 4-5", "1-3 & 5", "2-5", and the like. In addition, when a list of alternatives is positively provided, such listing can be interpreted to mean that any of the alternatives may be excluded, e.g., by a negative limitation in the claims. For example, when a range of "1 to 5" is recited, the recited range may be construed as including situations whereby any of 1, 2, 3, 4, or 5 are negatively excluded; thus, a recitation of "1 to 5" may be construed as "1 and 3-5, but not 2", or simply "wherein 2 is not included." It is intended that any component, element, attribute, or step that is positively recited herein may be explicitly excluded in the claims, whether such components, elements, attributes, or steps are listed as alternatives or whether they are recited in isolation.

Although $CF_3SO_2Im$ is available from several vendors, it is quite expensive at present. The inventor expected that the cost of $CF_3SO_2Im$ would be reduced if it can be made from $CF_3SO_2F$ in one step with one mole equivalent of gas.

There are no known reactions of $CF_3SO_2F$ with the ring nitrogen of any protic azoles such as imidazoles, pyrazoles, 1,2,4-triazoles, indazoles, benzimidazoles, or benzotriazoles. There are no known reactions of $CF_3SO_2F$ with the ring nitrogen of any N-silylimidazoles, N-silylpyrazoles, or N-silyl-1,2,4-triazoles, N-silylindazoles, N-silylbenzimidazoles, or N-silylbenzotriazoles either.

The present disclosure provides methods for producing triflazoles or related derivatives thereof, and the resulting triflazoles and/or derivatives thereof.

The terms "protic" and "aprotic" used herein refer to the presence or absence, respectively, of labile hydrogen atoms in a molecule. The term "protic" is used because the labile hydrogen atom often moves as a proton, but it does not have to be acidic in order to be protic. For example, diethylamine is both protic and a very weak acid. Its N—H hydrogen can only be removed with butyl lithium and the like, yet its N—H hydrogen is highly labile in many solvents. Protic hydrogen is mostly bound to nitrogen or oxygen atoms and aprotic hydrogen is mostly bound to carbon atoms. The term "aprotic solvent" is well-known and broadly refers to a solvent that has no —OH or —NH moieties. For example, ethyl ether and dimethylformamide are aprotic solvents, whereas ethanol and formamide are protic solvents.

Bases can be protic or aprotic. Triethylamine is an aprotic base and diethylamine is a protic base. Tetramethylguanidine is a protic base and pentamethylguanidine is an aprotic base. Some fluorides (NaF, KF, CsF) can act as aprotic bases. Anions (and cations) can be protic or aprotic. Bifluorides are protic. Carbonates are aprotic. Bicarbonates are protic. Hydroxides are protic. Alkoxides are aprotic.

Azoles can be protic or aprotic. Examples of aprotic azoles are thiazole and oxazole. Examples of protic azoles include, but are not limited to, imidazole, pyrazole, 1,2,4-triazole, benzimidazole, benzotriazole, indazole, 2-methylimidazole, 2-methylbenzimidazole, and 3,5-dimethylpyrazole. Protic azoles can be treated with base to give an aprotic azolate salt. Protic azoles are commonly referred to as "free azoles" and the terms are interchangeable. For example, "protic imidazole" and "free imidazole" both refer to the same chemical substance, formally named 1H-imidazole. Unless indicated otherwise, references to "azole" made herein will be understood to encompass protic azoles, not aprotic azoles.

The suffixes "Im", "Pz" "Tz", "BzIm", "BzTz" and "Me$_2$Pz" refer to the radical base structures of imidazole, pyrazole, 1,2,4-triazole, benzimidazole, benzotriazole, and 3,5-dimethylpyrazole, respectively, and are appended to prefixes of trifluoromethanesulfonyl and silyl radicals to give abbreviated terms, as described immediately below.

The prefix "$CF_3SO_2$" herein refers to the trifluoromethanesulfonyl radical. Hence, "$CF_3SO_2F$" refers to trifluoromethanesulfonyl fluoride, "$CF_3SO_2Im$" refers to 1-(trifluoromethanesulfonyl)imidazole, and so forth.

The prefix "$Me_3Si$" herein refers to the trimethylsilyl radical. For example, "$Me_3SiIm$" refers to 1-(trimethylsilyl)imidazole, "$Me_3SiF$" refers to fluorotrimethylsilane, and so forth.

The term "triflazole" herein refers generally to an N-(trifluoromethanesulfonyl)azole.

Unless indicated otherwise, references to "pot" made herein refer to a flask, autoclave, or other vessel used to conduct a reaction, or to hold the transferred contents of a reaction.

The term "reactive fluoride" herein refers to a fluorine atom or ion, within a compound, that can react with an N-silylazole to produce a fluorosilane and an azole anion compound.

Unless indicated otherwise, references to "low pressure" made herein refer to a condition at or below atmospheric pressure. Unless indicated otherwise, references to "high pressure" made herein refer to a condition above atmospheric pressure. The term "under pressure" can be used to describe unspecified high pressure.

The term "iced" used herein refers to the process of cooling a pot in a mixture of ice and water, to a temperature range of 0 to +5° C., unless otherwise specified.

The term "GCMS" used herein refers to the analysis method of gas chromatography-mass spectroscopy. Mass-to-charge values are reported with the term "m/e" followed by an integer. Mass detection was by electron impact.

In accordance with some embodiments, the present disclosure provides methods for producing triflazoles and related derivatives thereof, and resulting products.

In a broader aspect, the inventor has found at least two exemplary methods for producing triflazoles or related derivatives thereof.

In the first exemplary method, as illustrated in FIG. 1, $CF_3SO_2F$ is reacted with an azole or an azolate salt, to produce a triflazole. Such a reaction is optionally performed in the presence of an aprotic solvent. Pot temperatures below 50° C. are preferred. $CF_3SO_2F$ is reacted with an azole or an azolate salt at any pressure. In some embodiments, $CF_3SO_2F$ is reacted with an azole at a pressure at or below atmospheric pressure. The triflazole can be isolated.

Any suitable protic azole may be used. Examples include, but are not limited to, imidazole, benzimidazole, pyrazole, 1,2,4-triazole, benzotriazole, indazole, 2-methylimidazole, 2-methylbenzimidazole, and 3,5-dimethylpyrazole. The descriptions apply to all the azoles in each exemplary method described herein.

The reaction or reactions described herein may be optionally in the presence of an aprotic solvent. Examples of suitable aprotic solvents include, but are not limited to, acetonitrile, dichloromethane, ethyl ether, tetrahydrofuran, 2-methyltetrahydrofuran, methylcyclopentyl ether, methyl tert-butyl ether, propionitrile, butyronitrile, toluene, saturated hydrocarbon solvents such as hexane, heptane, pentane, cyclohexane, decalin, the like, and any combination thereof. The reactants may be suspended or dissolved in the solvent in some embodiments.

In some embodiments, the azolate salt has a metal cation. Examples of a suitable metal include, but are not limited to, lithium, sodium, potassium, cesium, magnesium, and a combination thereof.

In some embodiments, the azolate salt is derived from the protic azole and a metallic base such as a metal hydride, a metal alkoxide, a metal hydroxide, a metal carbonate, a metal fluoride, alkyllithiums, Grignard reagents, and a combination thereof.

In some embodiments, the azolate salt is derived from the protic azole and a metal carbonate. Examples of the metal in the metal carbonate include, but are not limited to, lithium, sodium, potassium, cesium, and magnesium. The derivation can be made separately or in situ.

In some embodiments, the azolate salt is derived from the protic azole and a metal fluoride. Examples of the metal in the metal fluoride include sodium, potassium and cesium. The derivation can be made separately or in situ.

In some embodiments, the azolate salt is derived from the protic azole and an aprotic organic base, or the protic azole as the base. Examples of a suitable aprotic organic base include, but are not limited to, alkylamines such as triethylamine and the like, 1,8-diazabicyclo(5.4.0)undec-7-ene (DBU), heteroaromatic amines such as pyridine, 4-(dimethylamino)pyridine and the like, aprotic guanidines such as pentamethylguanidine, tetramethyl-tert-butylguanidine, 1-methyl-1,3,4,6,7,8-hexahydro-2H-pyrimido[1,2-a]pyrimidine, 1-methyl-2,3,5,6-tetrahydro-1H-imidazo[1,2-a]imidazole, and the like, phosphazenes, and a combination thereof.

Figure 2:
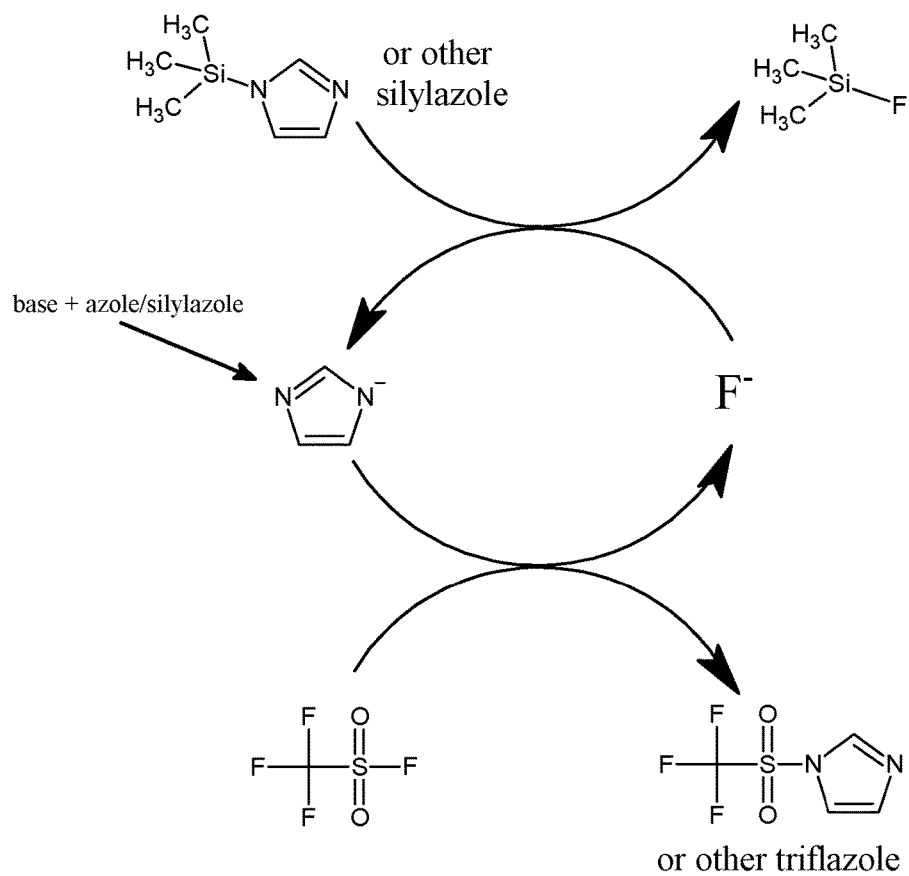
FIG. 2 illustrates an exemplary method for preparing a triflazole in accordance with some embodiments.

In the second exemplary method, as illustrated in FIG. 2, a triflazole is derived from an N-silylazole. In some embodiments, the N-silylazole is an N-(trialkylsilyl)azole. In some embodiments, the N-(trialkylsilyl)azole is an N-(trimethylsilyl)azole. The azole base structure may be derived from any suitable azole. Examples include, but are not limited to, imidazole, benzimidazole, pyrazole, 1,2,4-triazole, benzotriazole, indazole, 2-methylimidazole, 2-methylbenzimidazole, and 3,5-dimethylpyrazole, and substituted derivatives thereof. The descriptions apply to all the azoles in each exemplary method described herein.

In some embodiments, the triflazole is obtained by reaction of $CF_3SO_2F$ with an N-silylazole in the presence of a catalyst.

In some embodiments, the triflazole is obtained by reaction of $CF_3SO_2F$ with an N-silylazole in the presence of a basic catalyst.

In some embodiments, such a basic catalyst is the protic azole itself, or its azolate anion compound.

In some embodiments, such a basic catalyst is an aprotic base. Examples of suitable basic catalysts include, but are not limited to, aprotic organic bases, and a combination thereof.

In some embodiments, examples of suitable aprotic organic bases for use as a catalyst include, but are not limited to, tertiary amines such as triethylamine and the like.

In some embodiments, examples of suitable aprotic organic bases for use as a catalyst include, but are not limited to, bicyclic amidines and isothioureas such as 1,8-diazabicyclo(5.4.0)undec-7-ene (DBU), 2,3,5,6,7,8-hexahydro-imidazo[1,2-a]pyridine (DBN), 2,3,6,7-tetrahydro-5H-thiazolo[3,2-a] pyrimidine (THTP), and the like. A partial list of such bicyclic amidines and isothioureas is given by Birman et al. (Birman, V. B.; Li, X.; Han, Z. Organic Letters 2007, 9, 37-40), which is incorporated by reference in its entirety.

In some embodiments, examples of suitable aprotic organic bases for use as a catalyst include, but are not limited to, heteroaromatic amines such as pyridine, 4-(dimethylamino)pyridine, 1-methylimidazole, and the like.

In some embodiments, examples of suitable aprotic organic bases for use as a catalyst include, but are not limited to, phosphazene bases such as N'''-tert-butyl-N,N,N',N',N'',N''-hexamethylphosphorimidic triamide (i.e., t-BuN=P[NMe$_2$]$_3$), N,N,N',N',N'',N'',N'''-heptamethylphosphorimidic triamide (i.e., MeN=P[NMe$_2$]$_3$), and the like.

In some embodiments, examples of suitable aprotic organic bases for use as a catalyst include, but are not limited to, aprotic guanidines such as pentamethylguanidine, tetramethyl-tert-butylguanidine, 1-methyl-1,3,4,6,7,8-hexahydro-2H-pyrimido[1,2-a]pyrimidine (MeTBD), 1-methyl-2,3,5,6-tetrahydro-1H-imidazo[1,2-a]imidazole, and the like.

Further examples of suitable basic catalysts include, but are not limited to, the carbonates of lithium, sodium, potassium, magnesium, and cesium.

Further examples of suitable basic catalysts include, but are not limited to, metal hydrides, alkyllithiums, Grignard reagents, and a combination thereof.

Further examples of suitable basic catalysts include, but are not limited to, a hydroxide or alkoxide anion compound. These include, but are not limited to, potassium hydroxide, potassium tert-butoxide, tetramethylammonium hydroxide, tetraethylammonium hydroxide, tetrabutylammonium hydroxide, and the like.

Further examples of suitable basic catalysts include, but are not limited to, a trialkylsilyloxide anion compound. These include, but are not limited to, potassium trimethylsilyloxide (KOSiMe$_3$), tetramethylammonium trimethylsilyloxide, tetraethylammonium trimethylsilyloxide, and the like.

Further examples of suitable catalysts include, but are not limited to, compounds which contain reactive fluoride.

In some embodiments, examples of suitable catalysts which contain reactive fluoride are the fluorides or bifluorides of sodium, potassium, cesium, and tetraalkylammonium, such as tetraethylammonium bifluoride, tetraethylammonium fluoride, and the like.

In some embodiments, examples of suitable catalysts which contain reactive fluoride are that certain class of anion compounds containing unbound or "naked" fluoride as the anion. Examples of naked fluoride anion compounds include tetramethylammonium fluoride, tetrabutylammonium fluoride, phosphazenium fluorides such as [P(NMe$_2$)$_4$]$^+$F$^-$ (i.e., tris(dimethylamino)-N,N-dimethyl-$\lambda^5$-phosphaniminium fluoride), and the like.

In some embodiments, examples of suitable catalysts which contain reactive fluoride are anion compounds containing a pentavalent or hexavalent silicon, sulfur, tin, or other main-group anion complex, having at least one fluorine atom in the anion, such as tris(dimethylamino)sulfonium difluorotrimethylsilicate, tris(dimethylamino)methylium difluorotrimethylsilicate, tetrabutylammonium difluorotriphenylsilicate, tetrabutylammonium difluorotriphenylstannate, and the like.

In some embodiments, examples of suitable catalysts which contain reactive fluoride are compounds containing a reactive sulfur-fluorine or phosphorus-fluorine bond such as sulfur tetrafluoride, methyl sulfur trifluoride, dimethylsulfur difluoride, (diethylamino)sulfur trifluoride, phenylsulfur trifluoride, phenylsulfur pentafluoride, phosphorus trifluoride, phosphorus pentafluoride, and the like.

In some embodiments, examples of suitable catalysts which contain reactive fluoride are cation compounds containing a sulfur-fluorine bond in the cation, such as (diethylamino)difluorosulfonium tetrafluoroborate, (4-morpholinyl)difluorosulfonium tetrafluoroborate, and the like.

In some embodiments, examples of suitable catalysts containing reactive fluoride are activated geminal difluorides such as 2,2-difluoro-1,3-dimethylimidazolidine, 1,1-difluoro-N,N,N',N'-tetramethylmethanediamine, and the like.

In some embodiments, a tetravalent organosilicon compound such as fluorotrimethylsilane (Me$_3$SiF), tetramethylsilane (Me$_4$Si), ethyltrimethylsilane (EtSiMe$_3$), difluorodiethylsilane (Et$_2$SiF$_2$), and the like, can be added to the pot. These organosilanes can reversibly bind to fluoride, dissolve it as a coordination complex, and increase its reactivity.

In some embodiments, when a metallic cation compound is used as the catalyst, a crown ether such as 18-crown-6, 15-crown-5, and the like, can be added to the pot to make a more potent catalyst than the metallic cation compound alone.

In another aspect, the present disclosure provides a triflazole. The azole is derived from a protic azole base selected from the group consisting of pyrazole, 1,2,4-triazole, benzimidazole, benzotriazole, indazole, 2-methylimidazole, 2-methylbenzimidazole, and 3,5-dimethylpyrazole. Examples of a resulting compound include, but are not limited to, 1-(trifluoromethanesulfonyl)-1,2,4-triazole, 1-(trifluoromethanesulfonyl)benzimidazole, 1-(trifluoromethanesulfonyl)benzotriazole, 1-(trifluoromethanesulfonyl)pyrazole, 1-(trifluoromethanesulfonyl)-2-methylimidazole, and 1-(trifluoromethanesulfonyl)-3,5-dimethylpyrazole.

Reaction of CF$_3$SO$_2$F with Protic Azoles.

In some embodiments, CF$_3$SO$_2$F is introduced at low pressure into a sealed vessel containing an acetonitrile solution of imidazole and a suspension of a metallic base such as a metal carbonate or fluoride under anhydrous conditions. The dissolved imidazole exists in equilibrium with its anion, presumably at or near the surface of the solid. Some freely dissolved imidazolate may also be present. Addition of CF$_3$SO$_2$F to the pot results in an exothermic reaction. In theory, the ratio of moles of imidazole:carbonate and imidazole:fluoride are 1:1 and 1:2 respectively. In practice, excess carbonate or fluoride is preferred. The reaction may be preferably performed at temperatures from −10° C. to +50° C. Pot loads as high as 2 molar imidazole, or higher, may be employed. However, 2 molar imidazole is fully dissolved in acetonitrile only above about 20° C. At the end of the reaction, the insoluble salts are separated, the solvent is removed, and the product is distilled. High pressure may be used if the pot is well cooled; however, the use of low pressure means better safety, and also enables the use of large reactors for the same capital cost as a much smaller autoclave. In addition the use of low pressure allows for better temperature control and more precise endpoints, thus minimizing any excess of added CF$_3$SO$_2$F.

In some embodiments, imidazole is fully deprotonated prior to addition of CF$_3$SO$_2$F, and the resultant imidazolate salt is used. Suitable cations for the imidazolate anion include lithium, sodium, potassium, cesium, and magnesium. Sodium imidazolate is preferred. It is readily prepared in anhydrous form from imidazole and sodium hydroxide by heating under dynamic vacuum to 200° C. and <50 Pa. This treatment gives a friable solid which readily forms a fine suspension in acetonitrile. When the pot is evacuated prior to addition of CF$_3$SO$_2$F, the addition proceeds rapidly at low pressure. The pot is kept at the process temperature by cooling. In some embodiments, conducted at low pressure, when a fully deprotonated metal imidazolate is used and the pot properly degassed prior to addition of $CF_3SO_2F$, the pot pressure near the endpoint can drop below the vapor pressure of the pure solvent.

In some embodiments, where imidazole is allowed to react with $CF_3SO_2F$, aprotic organic bases are used stoichiometrically.

In some embodiments, where imidazole is allowed to react with $CF_3SO_2F$, $CF_3SO_2Im$ is the desired product, and an aprotic organic base is used, an excess of imidazole can be beneficial.

In some embodiments, where imidazole is allowed to react with $CF_3SO_2F$, $CF_3SO_2Im$ is the desired product, and an aprotic organic base is used, DBU or aprotic guanidines can be preferred. These strong bases can be used at low pressure. Unlike DBU, aprotic guanidines can be recycled by treatment with aqueous hydroxide, whereas DBU cannot be so recycled and is a one-time-use reagent.

In some embodiments, where imidazole is allowed to react with $CF_3SO_2F$, and $CF_3SO_2Im$ is the desired product, triethylamine can be preferred as a base. In some embodiments, where imidazole is allowed to react with $CF_3SO_2F$, the use of dichloromethane and triethylamine, at high pressure, can be preferred.

In some embodiments, where other azoles besides imidazole are used, the azole or azolate salt can be reacted with $CF_3SO_2F$ to produce other triflazoles, under the sets of conditions above described for imidazole. For example, metal salts of pyrazole, 1,2,4-triazole, benzimidazole, and benzotriazole can be used to produce TfPz, TfTz, TfBzIm, and TfBzTz respectively. Metal salts of these and other azoles can be used if they are anhydrous. Some azoles can be readily deprotonated with sodium or potassium hydroxide to give the anydrous azolate. Other anhydrous azolates are not easily obtained by simple reaction of the azole with sodium or potassium hydroxide. In such cases, a stronger base such as sodium or potassium tert-butoxide, a Grignard reagent, metal hydride, or alkyllithium can be used instead.

In some embodiments, reactors made of metal or plastic are preferred over glass, which corrodes in the presence of fluoride.

Reaction of $CF_3SO_2F$ with N-Silylazoles.

In some embodiments, $CF_3SO_2F$ is allowed to react with an N-silylazole. The reaction may be conducted without solvent or catalyst, but either or both can be preferred.

In some embodiments, where $CF_3SO_2F$ is allowed to react with an N-silylazole, N-(trimethylsilyl)azoles are preferred. When the N-silylazole is $Me_3SiIm$, the products are $CF_3SO_2Im$ and $Me_3SiF$.

In some embodiments, where $CF_3SO_2F$ reacts with an N-silylazole, a basic catalyst can be used, producing a catalytic cycle, as shown in FIG. 2. Strong bases can be used at low pressure. The aprotic strong base DBU is a preferred catalyst. DBU has a fairly low cost and is miscible with polar solvents and all of the neat liquid N-silylazoles tested to date. DBU is a very potent catalyst in the reaction of $CF_3SO_2F$ with N-silylazoles. The mole ratio of DBU:azole can be as low as 0.001:1, or lower, depending on the azole and the cooling power of the pot. Aprotic guanidines can also be preferred. Aprotic guanidines cost more than DBU, but they too are potent catalysts, are more heat-resistant than DBU, and can if necessary be recycled by treatment with aqueous hydroxide, unlike DBU.

In some embodiments, a weak base such as triethylamine is used. In these embodiments, high pressure, elevated temperature, or both, can be beneficial.

It is unclear whether or not the DBU or aprotic guanidine is reacting directly with the N-silylazole, or is simply deprotonating traces of free azole. A small amount of free azole can be added to the pot. To date this has not been necessary.

In some embodiments, a solvent-free reaction is most preferred. For example, the low pressure reaction of $CF_3SO_2F$ with neat $Me_3SiTz$/DBU (Example 1) or $Me_3SiIm$/DBU (Example 2) gives a 97% yield of product.

In some embodiments, when neat $Me_3Si$-azoles are allowed to react with $CF_3SO_2F$ at low pressure, the pot temperature is kept down so that the vapor pressure of byproduct $Me_3SiF$ (bp=16.4° C.) does not force the pot above atmospheric.

In some embodiments, the best yields are obtained by the use of aprotic reactants and catalysts.

In all embodiments, the best yields are obtained by the use of anhydrous reactants, catalysts, and solvents throughout the entire process.

EXPERIMENTAL

All reactions were conducted in a fume hood. Low pressure additions were conducted with a pressure gate, which regulates the pot pressure. When the pot pressure dropped below the set pressure, more gas was added until the set pressure was reached. The pressure gate display was also used as a manometer. Reaction progress was often monitored by GCMS, which is definitive for the identity of each peak in the trace, but only qualitative for its relative amount in the pot. When a liquid product was obtained, removal of more-volatile components of the reaction was omitted from the Example, and only the product boiling point is reported. N-silylazoles were prepared by reaction of the azole with hexamethyldisilazane.

EXAMPLE 1: 1-(Trifluoromethanesulfonyl)-1,2,4-triazole ($CF_3SO_2Tz$): A 250 mL, 1-necked round-bottom flask was equipped with a gas inlet and thermometer, and charged with 1-trimethylsilyl-1,2,4-triazole ($Me_3SiTz$, 79 grams, 0.56 moles) and diazabicyclo[5.4.0]undec-7-ene (DBU, 0.44 grams, 2.9 mmoles). The pot was iced and evacuated to a constant static pressure (1.3 kPa). Trifluoromethanesulfonyl fluoride ($CF_3SO_2F$, 92.6 grams, 0.609 moles) was added with stirring at low pressure over one hour at 5-16° C. The volatile byproduct, fluorotrimethylsilane ($Me_3SiF$), was distilled off at low pressure using a 40° C. water bath. The residue distilled at 63° C./2 kPa to yield the product $CF_3SO_2Tz$ (109.4 grams, 0.54 moles, 97%). GCMS m/e 201, single peak.

EXAMPLE 2: 1-(Trifluoromethanesulfonyl)imidazole ($CF_3SO_2Im$). A 250 mL, 1-necked round-bottom flask was equipped with a gas inlet and thermometer, and charged with 1-(trimethylsilyl)imidazole ($Me_3SiIm$, 57.9 g, 0.41 moles) and DBU (0.26 grams, 1.7 mmoles). The pot was iced and evacuated to constant static pressure (1.3 kPa). $CF_3SO_2F$ (66.4 grams, 0.436 moles) was added with stirring at low pressure over 46 minutes at 3-11° C. The volatile byproduct, $Me_3SiF$, was distilled off at low pressure using a 40° C. water bath. The residue distilled at 40° C./1.3 kPa to yield the product $CF_3SO_2Im$ (79.7 grams, 0.4 moles, 97%). GCMS m/e 200, single peak.

EXAMPLE 3: $CF_3SO_2Tz$. A 600 mL stirred autoclave was charged with $Me_3SiTz$ (38.9 g, 0.28 moles), DBU (0.6 g, 0.004 moles), and acetonitrile (200 mL), sealed, iced, and evacuated to constant static pressure (4 kPa). $CF_3SO_2F$ (41.9 g, 0.276 moles) was added under pressure over one minute, and the pot rose from 2 to 17° C. The pot quickly dropped to low pressure and was stirred overnight at ambient temperature. The next morning, the pot, at 8° C./33 kPa, was evacuated and most of the volatiles (200 g) distilled at 6° C. and low pressure into a dry ice trap. The pot was then infilled with nitrogen, opened, and the contents distilled at 54-57° C./2-2.5 kPa to give the product $CF_3SO_2Tz$ (43 g, 0.21 moles, 78%) as a clear colorless liquid. GCMS m/e 201 with a trace of solvent.

EXAMPLE 4: $CF_3SO_2Im$. A one-liter 4-necked round-bottom flask was equipped with a gas inlet having a thermometer hole and connected to a bubbler, a thermometer, a large stir egg, a powder funnel, and stoppers. The flask was charged against a flow of nitrogen with fresh dried potassium carbonate ($K_2CO_3$, 138 g, one mole), and the funnel replaced with a septum. The $K_2CO_3$ was stirred and a solution of imidazole (35 g, 0.5 moles) in acetonitrile (400 mL) was transferred via cannula to the stirred pot. The septum was replaced with a stopper and the bubbler disconnected from the line. The pot was iced and evacuated to constant static pressure (4 kPa) at 5° C. $CF_3SO_2F$ (80 g, 0.53 moles) was added at 5-7° C./40-53 kPa over 30 minutes. At the end of the reaction the pot was infilled with nitrogen, the contents filtered in a fume hood, and the solid rinsed with acetonitrile (250 mL). The combined filtrates were fractionally distilled at 30° C./1.2 kPa to give a crude product (64 g, 0.32 moles, 63%), which was combined with other reactions and redistilled to give a purified product.

EXAMPLE 5: $CF_3SO_2Im$. A solution of imidazole (34 g, 0.5 moles) in 1.00 N NaOH (500 mL) in a 1-necked 1L round-bottom flask was concentrated to dryness and the residue heated at 200° C./13 Pa for thirty minutes. The pot was cooled under vacuum and infilled with nitrogen. The friable contents were scraped loose from the flask walls, a stir egg added, and the flask quickly sealed with a septum. Acetonitrile (250 mL) was transferred in via cannula, the pot stirred for a few minutes, and the septum replaced with a gas inlet. The pot was iced, evacuated to constant static pressure (5 kPa), and $CF_3SO_2F$ (80 g, 0.53 moles) was added over 75 minutes at 40-93 kPa. The last fifteen minutes of the addition were conducted without ice and the pot warmed. The pot was stirred overnight at room temperature. The next morning, the pot pressure had dropped to 36 kPa. The pot was evacuated, infilled with nitrogen, and the pot contents filtered. The filtration took several hours and a rubber dam was used. The filtrate distilled at 38° C./1 kPa to give a crude product (78.4 g, 0.39 moles, 78%), which was combined with other reactions and redistilled to give a purified product.

EXAMPLE 6: 1-(Trifluoromethanesulfonyl)benzimidazole ($CF_3SO_2BzIm$). A 500 mL three-necked round-bottom flask was equipped with a thermometer, stir egg, septum, a gas inlet, and a stopper. The pot was charged via cannula with a 37.6% w/w acetonitrile solution of $Me_3SiBzIm$ (156.6 g, 0.31 moles), DBU (0.3 g, 0.002 moles) and the septum replaced with a stopper. The pot was stirred, iced, and evacuated to a constant static pressure (4 kPa). $CF_3SO_2F$ (49 g, 0.32 moles) was added over 16 minutes at 5-15° C./40-53 kPa. The pot was stirred and iced another 30 minutes to 3° C./34 kPa, then evacuated to 6 kPa and infilled with nitrogen. An attempt to directly distill this material gave a solid and a liquid. The residue, substantially free of acetonitrile, was taken up in benzene (100 mL) and the solid filtered off, giving a clear colorless filtrate. This filtrate was distilled (56.5° C./0.6 Pa) to give the product $CF_3SO_2BzIm$ (72.2 g, 0.29 moles, 93%). GCMS m/e 250, single peak.

EXAMPLE 7: 1-(Trifluoromethanesulfonyl)benzotriazole ($CF_3SO_2BzTz$). A 250 mL one-necked round-bottom flask was equipped with a stir egg and sealed with a septum. $Me_3SiBzTz$ (59.9 g, 0.31 moles) and DBU (0.07 g, 0.5 mmoles) were transferred in via cannula. The septum was replaced with a gas inlet and the pot contents stirred, evacuated (0.1 kPa) and iced. $CF_3SO_2F$ (46.8 g, 0.31 moles) was added at 93 kPa over an hour. The pot turned yellow immediately. The iced pot was then evacuated to 0.3 kPa and the pot contents solidified. This crude solid (78.2 g, 0.31 moles, 99.5%) was lachrymatory and gave multiple GCMS peaks, but exhibited a sharp melting point, 37-37.2° C. Lit. m.p.=37° C.

EXAMPLE 8: 1-(Trifluoromethanesulfonyl)pyrazole ($CF_3SO_2Pz$). A 500 mL one-necked round-bottom flask was equipped with a stir egg and charged with $Me_3SiPz$ (63 g, 0.45 moles) and DBU (0.11 g, 0.7 mmoles), quickly sealed with a gas inlet, iced and evacuated to 0.4 kPa. To the stirred, iced pot was added $CF_3SO_2F$ (71.3 g, 0.47 moles) at 53-93 kPa over 24 minutes. The pot was stirred another 30 minutes on ice and the pressure dropped to 51 kPa. The pot was then evacuated to 0.8 kPa and the pot contents froze, then melted as the flask warmed up. The product $CF_3SO_2Pz$ was distilled at 48° C./1 kPa as a clear colorless liquid. Yield, 85.9 g (0.43 moles, 95%) GCMS m/e 200, single peak.

EXAMPLE 9: 1-(Trifluoromethanesulfonyl)-2-methylimidazole ($CF_3SO_2MeIm$). A 250 mL one-necked round-bottom flask was equipped with a stir egg and a septum, and charged with N-(trimethylsilyl)-2-methylimidazole ($Me_3SiMeIm$, 72.7 g, 0.47 moles) and DBU (0.6 g, 4 mmoles). The septum was replaced with a gas inlet. The pot was iced and evacuated to 0.3 kPa. $CF_3SO_2F$ (57.4 g, 0.38 moles) was added at 67-72 kPa over two hours The product distilled at 46° C./0.5 kPa as a colorless liquid containing some tiny needles in the distillate (66.8 g, 0.31 moles, 82% from $CF_3SO_2F$). GCMS m/e 214 as the dominant peak; also present, m/e 154, $Me_3SiMeIm$, and other small unidentified peaks. The product was not easily separable from the contaminants with further distillation.

EXAMPLE 10: $CF_3SO_2Tz$. A 600 mL stirred autoclave was charged with 1,2,4-triazole (22 g, 0.32 moles), potassium fluoride (40 g, 0.7 moles) and acetonitrile (300 mL), sealed, iced, and evacuated (4.5 kPa). $CF_3SO_2F$ (50.2 g, 0.33 moles) was added to the stirred pot over an hour at 8-24° C./73-80 kPa. The pot was then stirred another ten minutes and dropped to 8° C./46 kPa. The pot was then evacuated, infilled with nitrogen, and the contents filtered. The filtrate distilled at 44° C./1.2 kPa to give the product $CF_3SO_2Tz$ (30.3 g, 0.15 moles, 47%). The remaining pot solids (13 g) consisted mostly of triazole.

EXAMPLE 11: 1-(Trifluoromethanesulfonyl)-3,5-dimethylpyrazole ($CF_3SO_2Me_2Pz$). A 250 mL one-necked round-bottom flask was equipped with a stir egg and a septum, and charged via cannula with N-(trimethylsilyl)-3,5-dimethylpyrazole (65.2 g, 0.39 mole) and DBU (0.27 g, 0.004 mole). The septum was quickly replaced with a vacuum adapter, the pot evacuated to constant static pressure (0.4 kPa), and iced. $CF_3SO_2F$ (62.6 g, 0.0.41 moles) was added to the stirred, iced pot at 93 kPa over 20 minutes. The pot was stirred another 15 minutes on ice until the pressure stabilized (64 kPa). The volatiles were pumped off (3 kPa) while warming to room temperature. The pot contents were filtered to remove a small amount of solid and the clear colorless filtrate (85 g) was distilled at 56° C./0.16 kPa to give the pure product $CF_3SO_2Me_2Pz$ (82.3 g, 0.36 mole, 93%) as a clear, colorless liquid. GCMS m/e 228, single peak.

Although the subject matter has been described in terms of exemplary embodiments, it is not limited thereto. Rather, the appended claims should be construed broadly, to include other variants and embodiments, which may be made by those skilled in the art.

What is claimed is:

1. A method for preparing an N-(trifluoromethanesulfonyl) azole, comprising:
reacting trifluoromethanesulfonyl fluoride ($CF_3SO_2F$) with an N-silylazole, wherein the N-silylazole has an azole base structure, and the azole base structure is protic when in a free form; and
isolating an N-(trifluoromethanesulfonyl) azole having a formula of $CF_3SO_2$-azole.

2. The method of claim 1, wherein the azole base structure is selected from the group consisting of imidazole, pyrazole, 1,2,4-triazole, benzimidazole, benzotriazole, indazole, 2-methylimidazole, 2-methylbenzimidazole, and 3,5-dimethylpyrazole.

3. The method of claim 1, wherein the N-silylazole is an N-(trialkylsilyl)azole.

4. The method of claim 3, wherein the N-(trialkylsilyl)azole is an N-(trimethylsilyl)azole.

5. The method of claim 1, wherein $CF_3SO_2F$ is reacted with the N-silylazole in the presence of a catalyst.

6. The method of claim 5, wherein the catalyst comprises a compound containing reactive fluoride.

7. The method of claim 1, wherein $CF_3SO_2F$ is reacted with the N-silylazole in the presence of a basic catalyst.

8. The method of claim 7, wherein the basic catalyst is a protic azole or its azolate anion compound.

9. The method of claim 7, wherein the basic catalyst comprises an organic aprotic base selected from the group consisting of a tertiary amine, an aprotic amidine, an aprotic isothiourea, an aprotic phosphazene, an aprotic guanidine, and combinations thereof.

10. The method of claim 9, wherein the organic aprotic base is selected from diazabicyclo(5.4.0)undec-7-ene, pentamethylguanidine, and tetramethyl-tert-butylguanidine.

11. The method of claim 7, wherein the basic catalyst comprises a compound selected from the group consisting of a metal carbonate, a metal fluoride, a metal hydride, alkyllithium, a Grignard reagent, a hydroxide, an alkoxide anion compound, and a combination thereof.

12. The method of claim 7, wherein the basic catalyst comprises a compound containing reactive fluoride.

13. The method of claim 1, wherein $CF_3SO_2F$ is reacted with the N-silylazole in the presence of an aprotic solvent.

14. A method for preparing an N-(trifluoromethanesulfonyl) azole, comprising:
reacting trifluoromethanesulfonyl fluoride ($CF_3SO_2F$) with an azole or an azolate salt of the azole, wherein the azole in a free form is protic; and
isolating an N-(trifluoromethylsulfonyl)azole having a formula of $CF_3SO_2$-azole.

15. The method of claim 14, wherein the azole base structure is selected from the group consisting of imidazole, pyrazole, 1,2,4-triazole, benzimidazole, benzotriazole, indazole, 2-methylimidazole, 2-methylbenzimidazole, and 3,5-dimethylpyrazole.

16. The method of claim 14, wherein the azolate salt has a cation of a metal selected from the group consisting of lithium, sodium, potassium, cesium, magnesium, and a combination thereof.

17. The method of claim 14, wherein the azolate salt is derived from the azole and a metallic base selected from the group consisting of a metal hydride, a metal alkoxide, a metal hydroxide, a metal carbonate, a metal fluoride, an alkyllithium, a Grignard reagent, and a combination thereof.

18. The method of claim 14, wherein the azolate salt is derived from the azole and a metal carbonate, the metal being selected from the group consisting of lithium, sodium, potassium, cesium, magnesium, and a combination thereof.

19. The method of claim 14, wherein the azolate salt is derived from the azole and a metal fluoride, the metal being selected from the group consisting of sodium, potassium, cesium, and a combination thereof.

20. The method of claim 14, wherein the azolate salt is derived from the azole and an aprotic base, or the protic azole as the base.

21. The method of claim 14, wherein the azolate salt is derived from the azole and an aprotic organic base.

22. The method of claim 14, wherein $CF_3SO_2F$ is reacted with the azole or azolate salt at or below atmosphere pressure.

23. The method of claim 14, wherein $CF_3SO_2F$ is reacted with the azole or the azolate salt in the presence of an aprotic solvent.

24. The method of claim 23, wherein the aprotic solvent is acetonitrile.

25. A compound being 1-(trifluoromethanesulfonyl)-3,5-dimethylpyrazole, or 1-(trifluoromethanesulfonyl)-2-methylimidazole.

* * * * *